(12) United States Patent
Kagermeier et al.

(10) Patent No.: US 8,405,490 B2
(45) Date of Patent: Mar. 26, 2013

(54) WIRELESS TRANSMISSION FOR A MEDICAL DEVICE

(75) Inventors: Robert Kagermeier, Nürnberg (DE); Dietmar Sierk, Erlangen (DE); Reiner Staab, Baiersdorf (DE); Susanne Elisabeth Staab, legal representative, Baiersdorf (DE); Katharina Staab, legal representative, Aschaffenburg (DE); Silvia Rachor, legal representative, Goldbach (DE)

(73) Assignee: Siemens Aktiengesellschaft, München (DE)

( * ) Notice: Subject to any disclaimer, the term of this patent is extended or adjusted under 35 U.S.C. 154(b) by 792 days.

(21) Appl. No.: 11/995,795

(22) PCT Filed: Jul. 5, 2006

(86) PCT No.: PCT/EP2006/063902
§ 371 (c)(1),
(2), (4) Date: Jan. 15, 2009

(87) PCT Pub. No.: WO2007/009881
PCT Pub. Date: Jan. 25, 2007

(65) Prior Publication Data
US 2009/0224935 A1 Sep. 10, 2009

(30) Foreign Application Priority Data
Jul. 20, 2005 (DE) .......................... 10 2005 033 957

(51) Int. Cl.
G08C 19/12 (2006.01)
(52) U.S. Cl. ................................... 340/13.24
(58) Field of Classification Search ............. 340/825.69, 340/825.72, 13.24
See application file for complete search history.

(56) References Cited

U.S. PATENT DOCUMENTS

| | | | |
|---|---|---|---|
| 6,563,430 B1 * | 5/2003 | Kemink et al. ............... 340/8.1 |
| 2003/0184475 A1 * | 10/2003 | Williams et al. .............. 342/465 |
| 2005/0033515 A1 * | 2/2005 | Bozzone ....................... 701/214 |
| 2005/0080566 A1 * | 4/2005 | Vock et al. ........................ 702/2 |
| 2005/0256675 A1 * | 11/2005 | Kurata ........................... 702/153 |
| 2006/0244627 A1 * | 11/2006 | Kagermeier et al. .... 340/825.69 |

FOREIGN PATENT DOCUMENTS

EP 0 801 342 3/1997
EP 1 429 217 A2 11/2003
(Continued)

OTHER PUBLICATIONS

German Office Action dated May 17, 2006 for DE 10 2005 033 957.3-55.
(Continued)

*Primary Examiner* — Daniel Wu
*Assistant Examiner* — Kam Ma
(74) *Attorney, Agent, or Firm* — Lempia Summerfield Katz LLC

(57) ABSTRACT

A system for wireless operation includes a receiver and a mobile remote control unit having an acceleration sensor and a control unit. The mobile remote control unit is operable to wirelessly transmit control signals to the receiver. The control unit is operable to receive and evaluate measurement signals of the acceleration sensor, determine a connection quality between the mobile remote control unit and the receiver, and block the transmission of at least some of the control signals when a decision criterion determined by the measurement signals of the acceleration sensor and the connection quality is exceeded.

16 Claims, 2 Drawing Sheets

FOREIGN PATENT DOCUMENTS

| | | | |
|---|---|---|---|
| EP | 1479964 | A2 | 11/2004 |
| EP | 1480180 | A1 | 11/2004 |
| WO | WO 00/17737 | | 3/1999 |
| WO | WO 2005/018242 | A2 | 2/2005 |
| WO | WO 2005018242 | A2 * | 2/2005 |

OTHER PUBLICATIONS

Written Opinion (with translation) (OF PCT/EP2006/063902).
International Search Report (of PCT/EP/2006/063902).
International Search Report (OF PCT/EP2006/063902).

* cited by examiner

WIRELESS TRANSMISSION FOR A MEDICAL DEVICE

The present patent document is a 35 U.S.C. §371 application of PCT Application Serial Number PCT/EP2006/063902 filed Jul. 5, 2006, designating the United States, which is hereby incorporated by reference. This patent document also claims the benefit of German Patent Application No. DE 10 2005 033 957.3 filed Jul. 20, 2005, which is hereby incorporated by reference.

BACKGROUND

The present embodiments relate to wireless transmission for a medical device.

With a medical diagnostic or therapy system, one or a number of medical devices are usually provided to treat a patient. The medical devices are operated by a control unit. For example, the device may be an x-ray diagnosis device or other device for medical purposes. For the doctor or the operating personal, it is often necessary to be able to operate the device from different spatial positions. Some of the devices have a remote control unit. To prevent damage from occurring as a result of the connecting cable between the remote control unit and the device, the control signals may be transmitted wirelessly. The control signals may be transmitted using infrared signals or radio signals.

The wireless transmission of control signals is reliably guaranteed within a defined region, for example, within an examination room. With the use of infrared signals, the transmission of the control signals through objects disposed between the infrared transmitter and the infrared receiver is prevented. Even with radio signals, the transmit signals can be negatively affected through objects disposed between the transmitter and receivers, since the transmission power may only be set up for limited coverage. An unintended actuation of the remote control unit, when the remote control unit is located outside the examination room, for instance, should not result in the device being operated. This is ensured with the use of infrared transmitters. When radio signals are used, an attempt is made to achieve this by limiting the transmit power. Limiting the transmit power can result in functional impairments also occurring within the room.

Measures of this type are not sufficient to ensure a safe and reliable operation and to exclude malfunctions. Wired operation continues to be employed for safety-critical operating functions.

WO 00/17737 A1 discloses a mobile control device for undertaking locally different control functions in the household. The device uses all acceleration sensor, for example, as a relative local sensor, to determine a current actual position of the control device, and to provide context-sensitive control information as a function of the actual position as well as to transmit context-sensitive control commands in a wireless fashion.

EP 1 429 217 A2 discloses a processing, measuring or transportation station. The station can be controlled wirelessly by a mobile control panel. The station includes a local connection facility that only allows the station to be controlled by the control panel when in an activated state. The local connection facility is activated when the signal emitted by the control panel is received with minimal signal strength by a receiver of the station.

EP 0 801 342 A2 discloses a user interface with a mobile data processing system. A geographic position of the data processing system is determined by acceleration sensors. One of these corresponding user environments is selected with the aid of the position determined and activated on the data processing system. The user interface is intended in particular for use in the medical field.

SUMMARY AND DESCRIPTION

The present embodiments may obviate one or more drawbacks or limitations inherent in the related art. For example, in one embodiment, a medical device may include a safe and reliable wireless operation.

In one embodiment, an apparatus (system) includes a mobile remote control unit (remote control) for the wireless transmission of control signals to a receiver.

An acceleration sensor is integrated into the remote control. The measurement signals of the remote control represent a measure for a translocation of the mobile remote control unit. The apparatus includes a control unit, which is integrated into the remote control. The control unit is designed to receive and evaluate measurement signals of the acceleration sensor.

The control unit is designed to determine the connection quality between the remote control and the receiver. The control unit evaluates the signal strength and bit error frequency in order to determine the connection quality. The bit error frequency is the relationship between the faulty and the non-faulty digital data. The evaluation of the connection quality allows a redundant safety to be achieved and an extended distance measurement.

The control unit is designed to determine a decision criterion on the basis of the measurement signals of the acceleration sensor and the connection quality. The decision criterion indicating whether the safety and reliability of the signals transmission is ensured. The control unit may block the transmission of control signals if it detects that the decision criterion has been exceeded, and that the safety and reliability of the signal transmission is no longer ensured.

The acceleration sensor may include a conventional micromechanical acceleration sensor, as is used in many technical fields. By integrating the acceleration sensor into the remote controller, a safety measure for ensuring the control function is developed with a minimal technical outlay. The transmission power can be safely set sufficiently high. No complex systems for position determination are required for the remote controller, for example, an expensive triangulation measurement with a number of base stations.

The acceleration sensor is embodied as a three-dimensional acceleration sensor, which detects the acceleration in all three spatial directions. The acceleration sensor system is designed such that rotational movements about the three spatial axes are detected.

The control unit is determines the current actual position of the remote controller in respect or a reference position, for example, in respect of the receiver or of a defined spatial position, from the measurement signals. The control unit determines, on the basis of the measurement values transmitted by the acceleration sensor, the actual position of the remote control unit within the room. A difference distance value is determined from the starting position as a inertial navigation. The current actual position is monitored so as to determine whether it lies within a permitted movement space.

To improve the accuracy of the position determination, an electronic compass is integrated into the remote control. The movement direction can be accurately determined with the electronic compass.

The remote control may include a memory for storing the actual position. The memory may make a reliable statement relating to the respective actual position at any time. The memory may ensure that a correct spatial starting point is used to determine the current actual position even after a rest phase and in the event of the remote control being moved again.

The remote control may include a reset element. The reset element can reset the current coordinates of the actual position, for example, to the coordinates of the reference position. As a result a readjustment is carried out. The reset element is a manual key, for example, which is actuated if the remote control is located in the reference position. Alternatively, the reset element can be realized in a control-specific fashion, if the remote control is plugged into a charging or base station at the site of the reference position, for example.

The connection quality between the remote control and the receiver can be evaluated (determined). To determine the connection quality, the signal strength and the bit error frequency is evaluated. The bit error frequency is the relationship between the faulty and the non-faulty digital data. A redundant safety is achieved by evaluating the connection quality and an extended distance determination is enabled if necessary.

The data for connection quality is expediently correlated with the measurement signals of the acceleration sensor. The value of the signal strength, such as the change in the signal strength, for example, the gradient, is used as data for the connection quality. An evaluation is carried out at the same time to determine whether the remote control is moving and whether a change in the signal strength occurs. In the case of the correlated evaluation, it is not necessary to determine the actual position of the remote control, but the actual position can be determined. The decision criterion, which, if exceeded, results in the transmission of the control signals being blocked, is determined in a first variant by the determined actual position or the distance value calculated from there to the reference position in combination with the connection value. In a second variant the decision criterion is determined by the correlation between the translocation and the connection quality and/or the change thereof. With the evaluation of the correlation between the translocation and the connection quality, the transmission of control signals is only blocked, for example, when a reduction in the connection quality is detected in conjunction with an impermissibly large translocation.

The transmission of the control signals are blocked if the current actual position is detected and a predetermined inventive value is exceeded. In other words, when a predetermined distance from the remote control to the reference position is exceeded the transmission of the control signals is blocked. This prevents any unintended control outside the permitted movement space for the remote control.

The transmission of at least selected control signals may be blocked when a predetermined connection value for the connection quality is not reached. The blocked transmission may prevent the device from failing as a result of a faulty signal transmission when the connection quality is poor. Provided adequate signal strength for clear signal evaluation still exists, the blockage may only occur at the same time if the predetermined distance value is exceeded. This measure allows operation within the permitted movement space even when the connection quality is negatively affected. Unlike safety which exclusively takes the connection quality as its measure, with this embodiment variant, the functionality is not impaired by objects which are located between the transmitter and the receiver.

The remote control may include a release element for the manual release of the blockage. The doctor or operating person has the freedom also to operate the device outside the permitted movement space. A conscious release is needed, so that an unintended operation can be excluded. The release element is a release button arranged on the remote control, for example, which has to be actuated and kept pressed during the operation. Alternatively, a time function is activated after brief activation of the release button or a release foot switch. The time function allows operation for a predetermined time span of 10 seconds, for example.

The device emits at least one warning signal. A number of different warning signals may be emitted. The warning signals make the operating person or the doctor aware of interferences or specific impermissible or critical situations. A first acoustic warning signal may be provided. The warning signal is emitted if the transmission is blocked and the remote control is simultaneously actuated in order to trigger specific, critical control signals. These control signals are in particular safety-relevant control signals. The acoustic warning signal allows the operating person to be made aware of the blockage immediately. The acoustic warning signal is expediently emitted exclusively with such critical, safety-relevant control signals.

A second warning signal may be provided. The second warning signal is emitted when a critical distance between the remote control unit and the receiver is achieved. The second warning signal is an optical signal, a flashing light on the remote controller, for example, in order to make the user aware of the connection quality being poor or the permitted movement space resulting therefrom.

A third warning signal is provided. The third warning signal may be acoustic. The third warning signal is emitted when the connection between the remote control and the receiver is interrupted. This prevents an unintended removal of the remote control unit.

The warning signals may be embodied such that the control person is made aware of non-critical situations by way of optical warning signals, for example, flashing light-emitting diodes. Acoustic warning signals are only emitted if the control person selects a blocked control function or takes the remote controller with them by mistake. This results in the entire safety mechanism being highly user-friendly.

In one embodiment, the control unit comprises a teaching (collaboration) function in order to determine the permitted movement space. Using the teaching function, the boundary of the permitted movement space is paced out with the remote control unit in order to define the permitted movement space and/or some selected boundary positions of the movement space are accepted with the remote control. By pressing a "Teach-in" key, for example, the current actual position is stored as a limit value of the movement space.

Using the acceleration sensor, extreme acceleration values are detected and registered. The extreme accelerations can be attributed to an impact or fall for instance. This information can be helpful in the case of guarantee claims, in order to be able to point to an inappropriate operation. The permanently stored acceleration values, which exceed a predetermined limit value, can be read out and evaluated with the aid of a diagnosis device which can be connected if necessary to an interface.

A method for the wireless operation is provided. The preferred embodiments and functions cited in respect of the device are transferred to the method. A method for wirelessly transmitting control signals to a receiver using a mobile remote control unit may be provided. The method may include detecting a translocation of the remote control unit with respect to a reference position using an acceleration sensor; determining the connection quality between the remote control unit and the receiver; determining a decision criterion on the basis of the translocation and the connection quality; and blocking the wireless transmission of the control signals if the decision criterion is exceeded.

BRIEF DESCRIPTION OF THE DRAWINGS

An exemplary embodiment is described in more detail below with reference to the drawings, in which.

DETAILED DESCRIPTION

Figure 1:
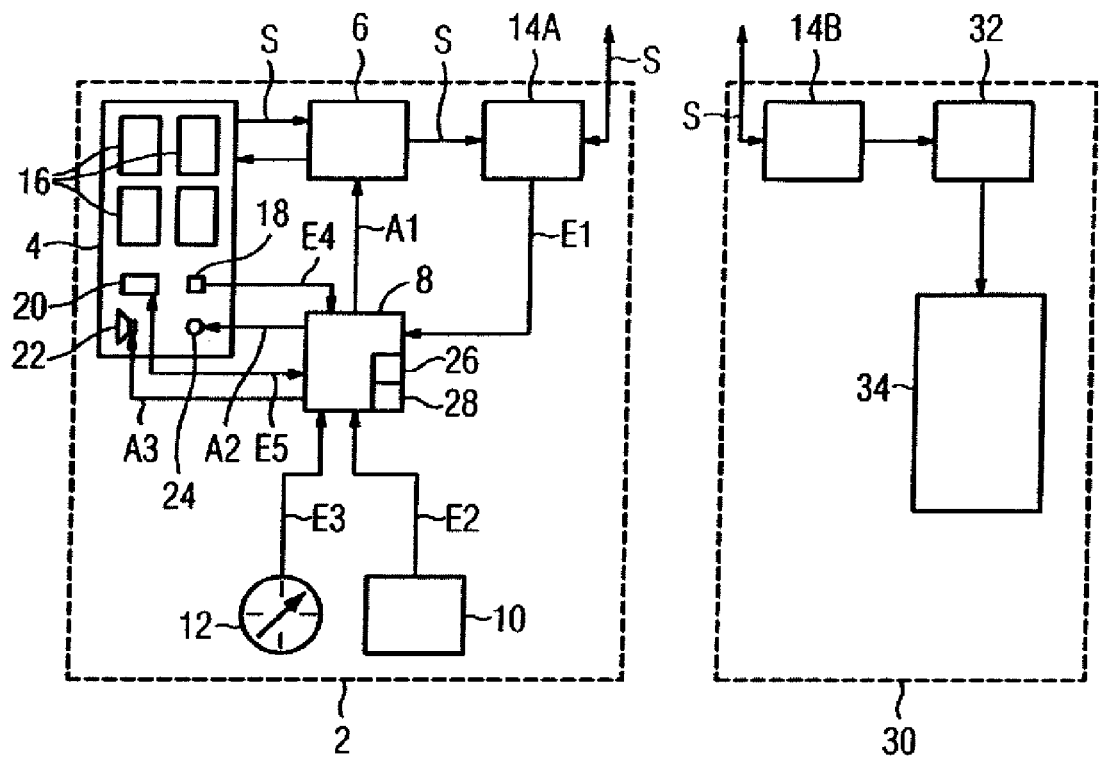
FIG. 1 shows one embodiment of a block diagram illustration of an apparatus for the wireless operation of a medical device.

Identical parts are provided with the same reference characters in the figures.

In one embodiment, as shown in FIG. 1, a remote controller 2 (indicated by dashed line) has a control panel 4 embodied as a keyboard, a keyboard controller 6, a control unit 8, a 3D acceleration sensor 10, an electronic compass 12, and a first radio module 14A embodied as a transmitter. In addition to operating keys 16, the control panel 4 has a reset element embodied as a reset button 18 and a release element 20. In the exemplary embodiment, an acoustic warning element embodied as a loudspeaker 22 and an optical warning element 24 embodied as an LED are integrated in the control panel 4.

The control unit 8 includes a microprocessor 26 and a memory 28.

The remote controller 2 allows a medical device 30 (indicated by a dashed line) to be actuated in a wireless fashion with the aid of radio signals. A second radio module 14B, which is embodied as a receiver, and a device controller 32 are integrated into the device 30. A component 34 of the device 30, for example, a radiation source of an x-ray device or a patient support (couch), is activated by the device controller 32.

For the remote controlled wireless operation of the device 30, a control signal S is transferred to the keyboard controller 6 by activating one of the control keys 16. A check is carried out (performed) in the keyboard controller 6 to determine whether a release signal A1 is present from the control unit 8. If the release signal A1 is present, the control signal S is forwarded to the first radio module 14A, which emits the control signal S as a radio signal. The radio signal is detected by the radio module 14B and transmitted to the device controller 32, which thereupon triggers a control function. The control function corresponds to the device controller 32, for example, a height adjustment of a patient support (couch) or an activation of a radiation source.

The two radio modules 14A, B are transmit and receive units. For example, the radio module 14A used as a transmitter for the control signals S simultaneously also receives signals from the second radio module 14B. The received signals are transmitted as input signals E1 to the control unit 8 to evaluate the connection quality. The control unit 8 also obtains measurement or input signals E2 to E5 from the acceleration sensor 10, electrical compass 12, the reset button 18, and the release element 20.

Output signals A1 to A3 are emitted from the control unit 8 to the keyboard controller 6, the optical warning element 24, and the loudspeaker 22. The output signal A1 may correspond to the release signal.

Figure 2:
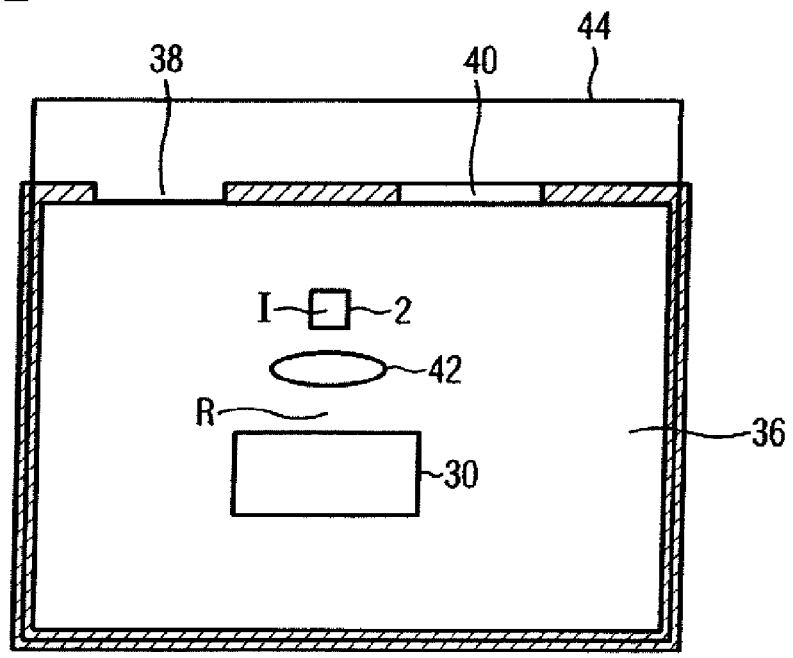
FIG. 2 shows one embodiment of a medical treatment room.

As can be seen from FIG. 2, the device 30 is arranged within a treatment room 36, which is accessible by a door 38 and has a window 40. The remote control 2 is also arranged in the treatment room 36. An obstruction 42 is arranged between the remote controller 2 and the device 30. With this constellation, a remote control using an infrared signal, would already not be possible. A permitted movement space 44 is shown in FIG. 2 by a rectangle. Operation by the remote control 2 is allowed within this movement space 44. The permitted movement space 44 is adjusted in the exemplary embodiment to the floor surface of the treatment room 36 and a sub region additionally extends across the front side of the treatment room 36, so that the device 30 can also be controlled from outside the treatment room 36 using eye contact through the window 40, for example.

To ensure a safe and reliable operation of the device 30 by the remote control 2, two control mechanisms that complement one another are provided. The first control mechanism detects the actual movement of the remote control 2 within the three-dimensional space, for example, both within the plane and in terms of height. With the aid of the second control mechanism, the connection quality between the two radio modules 14A, B is monitored. The second control mechanism may be used in addition to the first control mechanism. The two control mechanisms optionally or in combination with one another allow the following method and/or monitoring methods to be used. In one alternative embodiment, the current actual position is used with the aid of the first control mechanism. The value of the connection quality may be used. In another embodiment, the relative translocation is only determined instead of the actual determination of the actual position and the connection quality is set in correlation with the connection quality, such as in correlation with the change, for example, the gradient. Finally, a combination of these two alternatives is possible. All data available may be used to obtain the most accurate evaluation possible.

The first control mechanism may include the control unit 8, the acceleration sensor 10, the electrical compass 12, and a memory 28.

The acceleration sensor 10 detects acceleration and a translocation of the remote controller 2. In one alternative embodiment, the current actual position is determined herefrom with respect to a reference position R. Conclusions can be drawn both in respect of the reset paths as well as the proposed direction with the aid of signals E2 transmitted by the acceleration sensor 10, so that when the starting position is known, a current actual position I of the remote controller 2 is determined in each instance. In order to increase directional accuracy, the input signal E3 of the electrical compass 12 is used to determine the actual position I. The current coordinates of the actual position I are stored in the memory 28 in each instance. The zero point of the coordinate system may be determined by the reference position R.

Provided the actual coordinates of the remote control 2 move within the coordinates of the permitted movement space 44, the control unit 8 transmits the release signal A1 to the keyboard controller 6. If the control panel 16 is activated, the control signal S is transmitted directly to the device 30.

As soon as the remote control 2 leaves the permitted movement space 44; however, the keyboard controller 6 is blocked, for example, the release signal A1 is no longer present. The output signal A2 is simultaneously emitted to the optical warning element 24, so that the control person is optically made aware (notified) of the remote control 2 leaving the permitted movement space 44. If one of the control panels 16 is activated, the control signal S is not forwarded. Provided this is a non-critical control function, nothing more is done. If however, a specific, essential or safety-relevant function has been executed, an acoustic warning signal is emitted by the loudspeaker 22, in order to notify the operating personal that the remote control 2 is blocked. By activating the release element 20, the control person is able to eliminate the blockage for a short period and operate the device 30.

The reset button 18 is provided to adjust the actual position I in relation to the reference position R. For adjustment purposes, the remote control 2 is brought to the reference position R and the reset button 18 is activated. This resets of the actual coordinate values are to zero.

In order to freely define the permitted movement space 44, the control unit 8 includes a teaching (calibration) function, In order to freely define the movement space 44, the remote control 2 is brought to the corner points of the movement space 44, for example, and a teaching button is actuated so that the current actual coordinates of the movement space 44 are determined and stored in the memory 28.

In parallel to monitoring the movement using the first control mechanism, the connection quality is monitored continuously. If the remote control 2 is located within the movement space 44, the release signal A1 is also present when an assumption actually has to be made from one position of the remote controller 2 outside the movement space 44 on the basis of a decreasing connection quality. These measures stop negative effects, such as the obstruction 42, for example, from impairing the functionality.

As soon as a safety-relevant connection quality is exceeded; however, certain operating functions are blocked, for example, provided safety-relevant functions are actuated by the remote controller 2, these are not transmitted to counteract the risk of a faulty function on grounds of an inadequate data transmission. At the same time, the acoustic signal is emitted, so that the operating person is informed and is able to eliminate the blockage by the release element 20. The poor connection quality is previously indicated by the optical warning element 24.

The field or signal strength received by the radio module 14A and/or the bit error frequency are used in order to monitor the connection quality.

If no signal or no significant signal from the radio module 14B is detected by radio module 14A, this is assessed as a break in the radio connection and an acoustic signal is emitted again. The device 30 can no longer be operated, since the remote control 2 is located outside the transmission range.

In order to make the operating person aware of different statuses, a distinction is made in each instance between the acoustic and optical warning signals.

The device 30 can be remotely controlled using the described apparatus in a reliable, safe and user-friendly fashion. The apparatus described here can be used for devices outside the medical field, but within the medical field, patients can as a result be treated in a safer fashion without risking their health.

To be able to identify an inappropriate operation, acceleration values which exceed a predetermined limit value and indicate an extreme acceleration may be stored permanently in the memory 28. Extreme acceleration values of this type indicate an inappropriate operation, for example, dropping the unit or other extreme acceleration values caused by impacts. These extreme acceleration values stored in the memory 28 can be read out by an interface and evaluated by a diagnosis device, for example, within the scope of routine-specific maintenance works.

Figure 3:
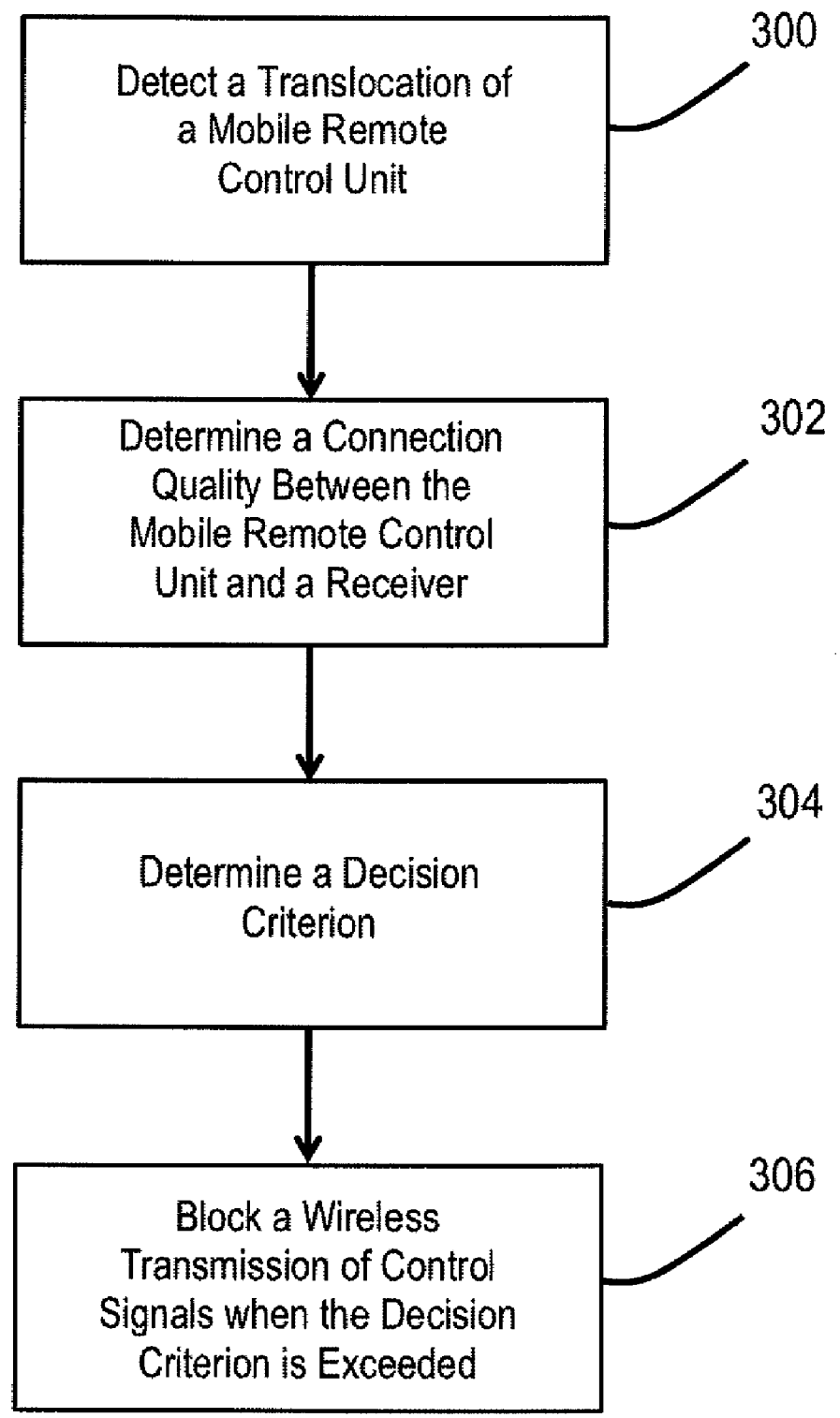
FIG. 3 shows a flowchart of one embodiment of a method for wirelessly transmitting control signals.

FIG. 3 shows a flowchart of one embodiment of a method for wirelessly transmitting control signals to a receiver using a mobile remote control unit. In act 300, a translocation of the mobile remote control unit with respect to a reference position is detected using an acceleration sensor. In act 302, a connection quality between the mobile remote control unit and the receiver is determined. In act 304, a decision criterion is determined on the basis of the translocation and the connection quality. In act 306, the wireless transmission of the control signals is blocked when the decision criterion is exceeded.

The invention claimed is:

1. A system for wireless operation comprising:
a receiver; and
a mobile remote control unit having an acceleration sensor and a control unit, the mobile remote control unit operable to wirelessly transmit control signals to the receiver,
wherein the control unit is configured to:
receive and evaluate measurement signals of the acceleration sensor;
determine a connection quality between the mobile remote control unit and the receiver;
block the transmission of at least some of the control signals when a decision criterion determined by the measurement signals of the acceleration sensor and the connection quality is exceeded;
determine, from the measurement signals of the acceleration sensor, a relative translocation of the mobile remote control unit;
correlate the relative translocation with a change in the connection quality; and
use the correlation as the decision criterion so that the transmission of at least some of the control signals is only blocked when a reduction in the connection quality is detected in conjunction with the determined relative translocation exceeding a permitted movement.

2. The system as claimed in claim 1, wherein the control unit is operable to determine a current actual position of the mobile remote control unit with respect to a reference position from the measurement signals of the acceleration sensor, the decision criterion being determined based on the current actual position and the connection quality.

3. The system as claimed in claim 2, wherein the control unit is operable to determine a distance between the current actual position and the reference position, the decision criterion being determined based on the distance and the connection quality.

4. The system as claimed in claim 1, wherein the mobile remote control unit includes an electronic compass.

5. The system as claimed in claim 2, further comprising a memory that is operable to store the current actual position.

6. The system as claimed in claim 2, further comprising a reset element operable to reset current coordinates of the current actual position.

7. The system as claimed in claim 1, wherein the control unit is operable to block the transmission of at least selected control signals of the control signals when a predetermined connection value for the connection quality is exceeded.

8. The system as claimed in claim 1, further comprising a release element operable to manually release the blockage.

9. The system as claimed in claim 1, wherein the control unit is operable to emit a first acoustic warning signal when the transmission is blocked, and the mobile remote control unit is actuated to trigger specific control signals of the control signals.

10. The system as claimed in claim 9, wherein the control unit is operable to emit a second warning signal when a critical distance is detected from the mobile remote control unit to the receiver.

11. The system as claimed in claim 10, wherein the control unit is operable to transmit a third warning signal when the connection between the mobile remote control unit and the receiver is interrupted.

12. The system as claimed in claim 1, wherein the control unit comprises a teaching function, with the aid of which a permitted movement space is determinable for the mobile remote control unit.

13. The system as claimed in claim 1, wherein detected acceleration values that exceed a predetermined limit value are registered for a subsequent diagnosis.

14. A method for wirelessly transmitting control signals to a receiver using a mobile remote control unit, the method comprising:
   determining a translocation of the mobile remote control unit with respect to a reference position using a measurement signal of an acceleration sensor;
   determining a connection quality between the mobile remote control unit and the receiver;
   determining a decision criterion on the basis of the measurement signal of the acceleration sensor and the connection quality; and
   blocking the wireless transmission of the control signals when the decision criterion is exceeded,
   wherein determining the decision criterion includes:
      correlating a change of the connection quality with the determined translocation; and
      using the correlation as the decision criterion so that the wireless transmission of the control signals is only blocked when a reduction in the connection quality is detected in conjunction with the determined translocation exceeding a permitted movement.

15. The method as claimed in claim 14, further comprising determining a current actual position of the mobile remote control unit with respect to the reference position on the basis of the detected translocation,
   wherein the decision criterion is determined on the basis of the current actual position and the connection quality.

16. The method as claimed in claim 15, further comprising determining a distance between the current actual position and the reference position,
   wherein the decision criterion is determined on the basis of the distance and the connection quality.

* * * * *